United States Patent [19]
Niklas

[11] 4,099,416
[45] Jul. 11, 1978

[54] RESOLUTION REAL-TIME ULTRASONIC IMAGING APPARATUS

[75] Inventor: Ludwig Niklas, Lovenich, Fed. Rep. of Germany

[73] Assignee: Krautkramer-Branson, Incorporated, Stratford, Conn.

[21] Appl. No.: 790,407

[22] Filed: Apr. 25, 1977

[51] Int. Cl.² .......................................... G01N 29/04
[52] U.S. Cl. ................... 73/602; 128/2 V; 73/620; 73/626
[58] Field of Search ............... 73/67.8 R, 67.8 S, 67.9, 73/67.7; 235/151.3; 340/5 MP, 1 R, 15.50 P; 128/2 V

[56] References Cited
U.S. PATENT DOCUMENTS

| | | | |
|---|---|---|---|
| 3,805,596 | 4/1974 | Klahr | 73/67.8 S |
| 3,885,224 | 5/1975 | Klahr | 73/67.8 S X |
| 3,991,607 | 11/1976 | Niklas | 73/67.7 |
| 4,012,952 | 3/1977 | Dory | 73/67.7 |

OTHER PUBLICATIONS

R. C. Eggleton, State-of-the-Art of Single Transducer Ultrasonic Imaging Technology, Medical Physics, Sep.-Oct. 1976, pp. 303-311.

*Primary Examiner*—Richard C. Queisser
*Assistant Examiner*—John P. Beauchamp
*Attorney, Agent, or Firm*—Ervin B. Steinberg; Philip J. Feig

[57] ABSTRACT

A real-time ultrasonic imaging system includes a display which is compensated for the non-ideal characteristics of the search beam profile. Echo responsive electrical signals are provided to a preprogrammed computing means for being processed to compensate for the characteristics of the test probe. The processed signals are displayed as being in focus at all distances from the probe, thereby resulting in an image exhibiting improved resolution.

14 Claims, 16 Drawing Figures

RESOLUTION REAL-TIME ULTRASONIC IMAGING APPARATUS

BRIEF SUMMARY OF THE INVENTION

The invention concerns an ultrasonic imaging system exhibiting improved image resolution. Specifically, a mathematical method and embodiment thereof are described which compensate the echo responsive electrical signals in a manner for simulating an ideal ultrasonic search signal. The resultant image presentation is in focus for defects or other acoustic discontinuities disposed within the workpiece at any distance from the surface.

When testing workpieces by the ultrasonic pulse-echo method the accuracy with which the location of a defect (acoustic discontinuity) disposed in the workpiece can be fixed is limited. The finite width of the ultrasonic energy search beam causes an ambiguity with respect to the depth location of the defect and the divergence of the search beam causes an ambiguity in the lateral position of the defect. Commercially available ultrasonic apparatus have sufficient depth resolution since the duration of the ultrasonic search pulse is maintained sufficiently short by the use of highly damped test probes as well as by amplifiers having adequate bandwidth. Physical characteristics, however, limit the sharpness of the ultrasonic energy search beam in the lateral direction. Probes having a small diameter provide a sharp beam directly in front of the probe, however the beam becomes very divergent at greater distance. If, in contrast, test probes of large diameter are used the divergence at the greater distances is much reduced, but immediately in front of the test probe the beam width is very broad.

In practice this disadvantage is often overcome by the use of a focussed sound beam. Within a predetermined focal distance the beam is sharp for providing a precise determination of the lateral position of a defect, however, in front of and behind the focal distance the beam width is greater than that of a non-focussed beam.

These effects manifest themselves particularly disadvantageous when a surface-like pictorial representation (display) in accordance with the B-scan method is desired (see J. and H. Krautkramer, "Ultrasonic Testing of Materials" (book), Springer Verlag, New York, New York, 1969, Chapter 2.353). The pictorial representation, when focussed probes are used, is very washed out in the lateral direction and is sharply defined only along a horizontal strip corresponding to the focal distance.

In accordance with the present invention, the above described shortcomings are avoided by initially producing an out-of-focus picture in a conventional way. In a second step, the known, or the readily determinable beam width is reduced by a mathematical method described hereafter to an ideally sharp beam to cause an ideally sharp pictorial representation of the workpiece at all distances from the probe.

In the following description one mathematical method proven in practice, is explained in greater detail. For ease of understanding the method is described for only a single line of the B-scan picture. If the entire B-scan presentation is to be improved, the described method will be repeated on a line-by-line basis. Further, a specially designed computer is described which can perform the mathematical process in real-time. This feature is particularly significant for application of this invention to the medical diagnostic field where real-time B-scan displays need to be observed which change synchronously with the heart beat. This requirement precludes the availability of extra time during which the computation process can occur.

A principal object of the present invention is, therefore, the provision of an ultrasonic scanning system including a specially designed computer for providing a focussed real-time display of an object being examined.

Another object of the invention is the provision of a specially designed computer for compensating echo responsive electrical signals commensurate with the characteristics of a transducer probe.

A further object of the invention is the provision of a method and apparatus for simulating an ideal probe to produce an image which is focussed at all distances from the probe.

Other and still further objects of the invention will become more clearly apparent when the following description is read in conjunction with the accompanying drawings.

BRIEF DESCRIPTION OF THE DRAWINGS

FIG. 1A is an elevational view of a test arrangement for testing a workpiece having point reflectors contained therein;

FIGS. 1B and 1C are graphical representation of the signals received by the probe in FIG. 1a;

FIG. 3A is an elevational view of a test arrangement for testing a workpiece having an extended reflector disposed therein;

FIGS. 3B and 3C are graphical representation of the signals received by the probe per FIG. 3a;

DETAILED DESCRIPTION OF THE INVENTION

Figure 1:
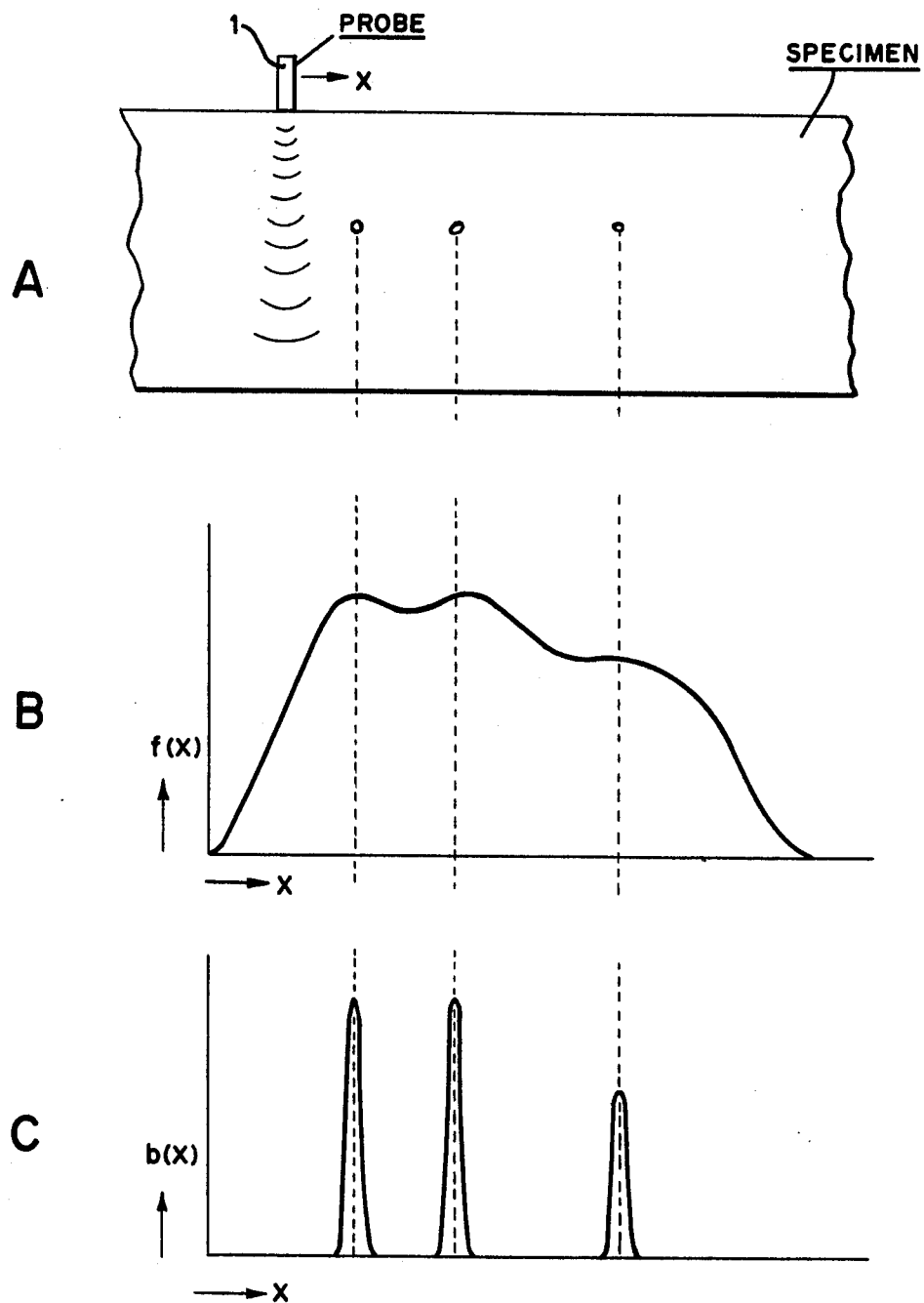

Referring to the drawings and in FIG. 1A in particular there is shown a workpiece containing three point reflectors disposed at a constant distance form the probe. The electroacoustic probe 1 (transducer) when energized transmits an ultrasonic search beam into the workpiece and receives echo signals arising from the search beam intercepting acoustic discontinuities (defects) disposed within the workpiece. A graph of the echo amplitude as a function of lateral displacement is shown in FIG. 1B. Due to the finite beam width of the search signals this curve is not clearly defined as contrasted with the desired ideal graph shown in FIG. 1C. It is possible to measure the lateral ambiguity by recording a single, isolated point reflector. The result of this latter test is the sound beam profile of the probe 1.

The invention concerns a mathematical method for transforming a curve in the form of FIG. 1B to the ideal graph in FIG. 1C, whereby it is assumed that the beam profile of the test probe is known or has been measured in a pretest.

Figure 2:
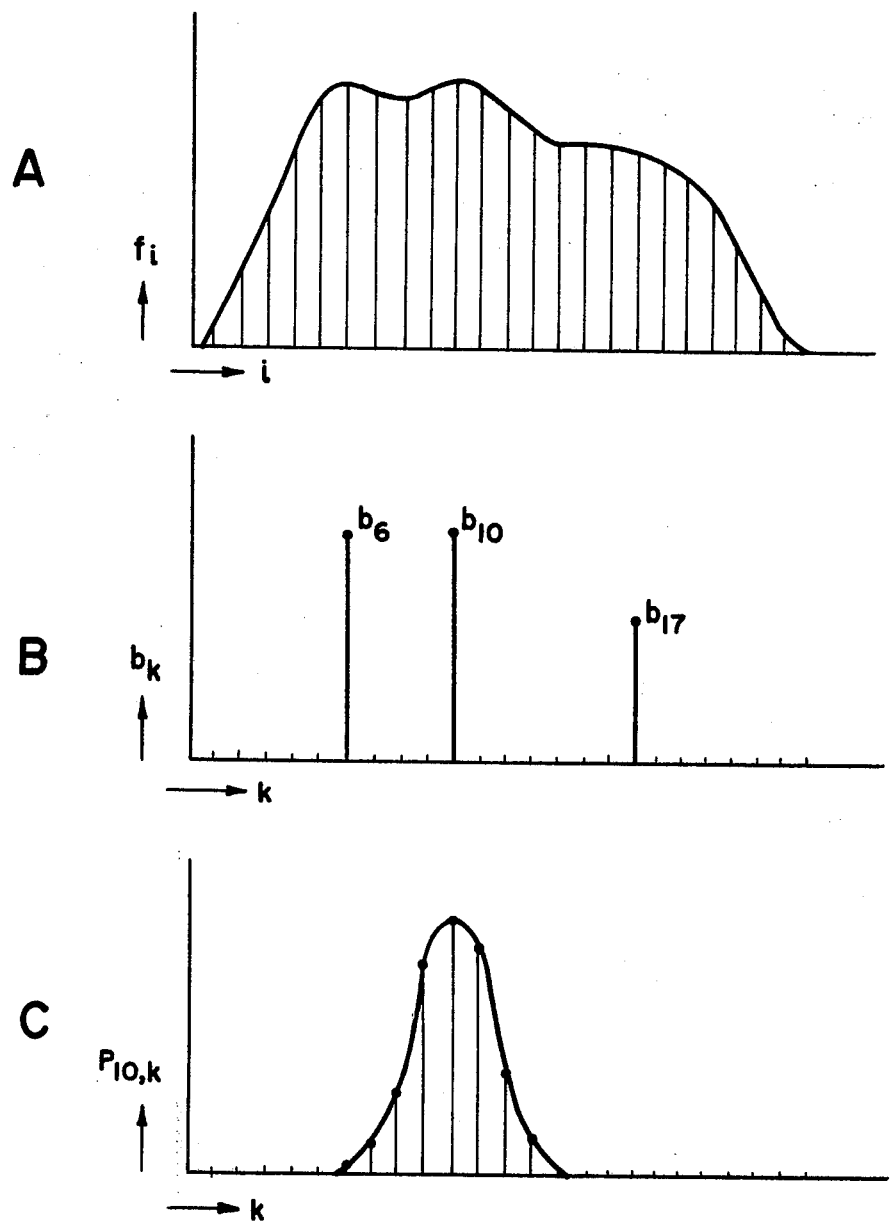
FIGS. 2A–2C are graphical representations of beam profiles.

In practice the graph per FIG. 1B is not available as a continuous curve but rather is a sequence of discrete echo amplitude values $f_i$ as shown in FIG. 2A. The expected ideal record per FIG. 2B is also a sequence of amplitude values $b_k$. If, in addition, the beam profile of the probe 1 is measured during a pretest, these values are a sequence $p_{ik}$ of amplitudes, whereby index $i$ is the position of the single point-test reflector and $k$ the probe position during this pretest. FIG. 2C shows such a $p_{ik}$-sequence, the reflector position being assumed to be at $i = 10$. If in this test the reflector would have another position, e.g. at $i = 8$, the sequence would be identical except for shift of two in the index $k$. That is $p_{10,k} = p_{8,k+2}$. The $p_{ik}$ sequence comprises elements of a matrix of the form:

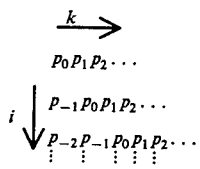

so that this matrix can be described solely by a simple sequence of $p_\nu$ values. The relation of $p_{ik}$ to $p_\nu$ is given by:

$$p_{ik} = p_\nu \text{ with } \nu = k - i \qquad \text{eq. 1}$$

If normal probes are used for scanning, the beam profile is symmetrical, which means $p_{-\nu} = p_{+\nu}$. If angle probes are used this is normally not the case. In the following equation this non-symmetrical type of beam profile is considered.

The instant disclosure makes use of the statement that the presentation of FIGS. 1B (2A) is a convolution of the ideal graph 1C (2B) of the beam profile:

$$f(x) = \int p(x - \xi) b(\xi) \, d\xi \qquad \text{eq. 2}$$

Figure 3:
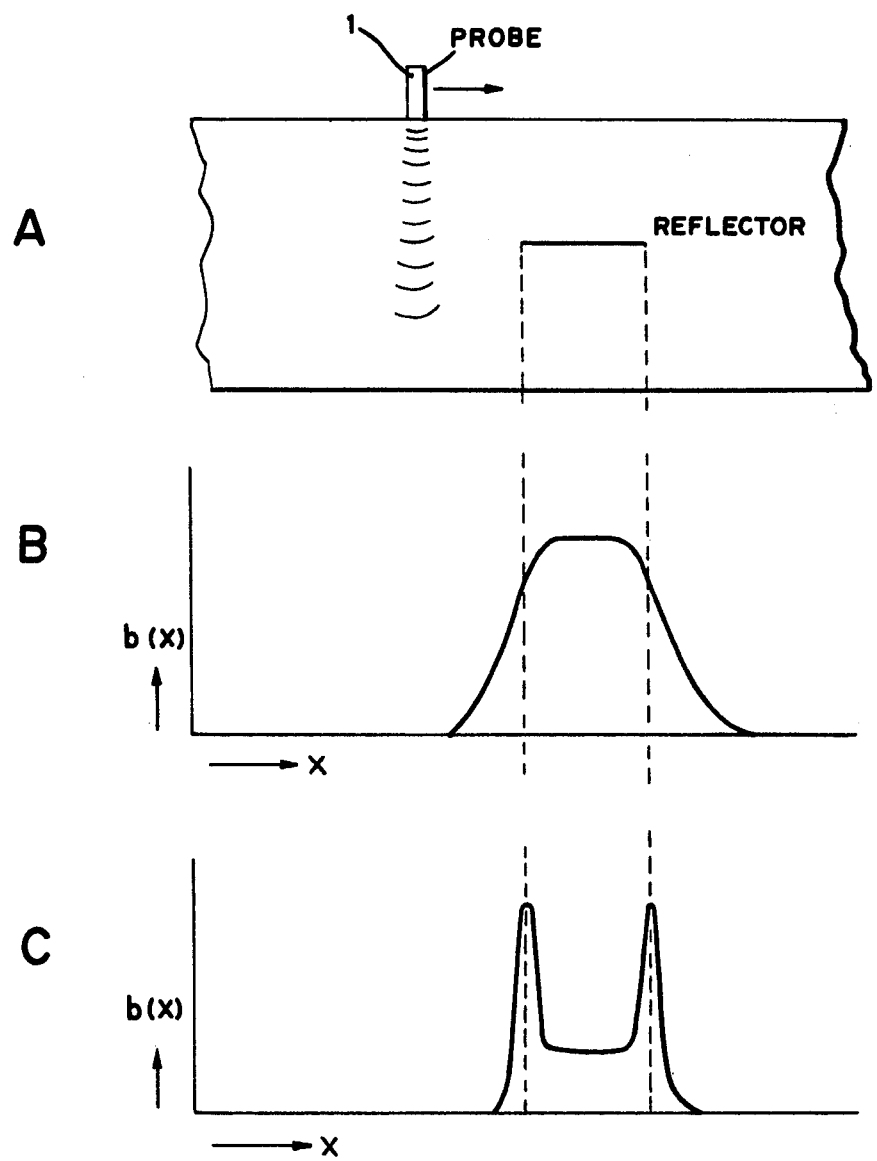

This statement is true in practice if the specimen FIG. 1A contains only isolated point reflectors. It is known that if an extended reflector of the type shown in FIG. 3A is present, the reflector can be described by an acoustic reflection from only the edges. Such fact is not in accordance with equation 2. Hence, the graph of the extended reflector per FIG. 3A is as shown by FIG. 3B. By use of the deconvolution method described below there results an ideal graph, and such result is shown as curve FIG. 3C. The beginning and the end of the reflector are emphasized in this graph, but such emphasis can be an advantage when the reflector size is measured.

If the values $f(x)$ (measured) in equation 2, $p(x)$ (profile) and $b(x)$ (ideal record) are given as a sequence of amplitude values the convolution integral in equation 2 changes to a system of linear equations:

$$f_i = \sum_k p_{ik} b_k; \quad i = 0,1,2,\ldots \qquad \text{eq. 3}$$

or using equation 1:

$$f_i = \sum_k p_{k-i} b_k \qquad \text{eq. 3a}$$

In equations 3 and 3a, $p_{ik}$ or $p_\nu$ is assumed to be known from pretesting and the values $b_k$ are unknown. To find these latter values, the inverse system of equations $$b_i = \sum_k d_{ik} f_k = \sum_k p_{ik}^{-1} f_k \qquad \text{eq. 4}$$

must be solved. In equation 4, the elements of the matrix $d_{ik}$ are the elements of the inverse matrix $p_{ik}^{-1}$. When inverting the $p_{ik}$ matrix it will be noted that the number of $p_{ik}$ elements is infinite.

There exists software programs for inverting matrices, but the required computing time is significant. The calculation must be done by approximating the infinite $p_{ik}$ matrix by a finite matrix. For reasons of accuracy the calculation must be done with matrices of many elements. To overcome this difficulty the following calculation method has been used with success.

Equation 4 can also be used to calculate the profile graph during the pretest measurements. In this case equation 4 is:

$$b_i = \begin{matrix} 1 \text{ for } i = 0 \\ 0 \text{ for } i \neq 0 \end{matrix}, f_k = p_\nu \qquad \text{eq. 5}$$

The $p_{ik}$ matrix has the special form shown in equation 1, it is also known that the corresponding inverse matrix has the same form. Therefore, the $d_{ik}$ matrix can be reduced to a sequence $d_\nu$:

$$d_{ik} = d_\nu \text{ with } \nu = k - i \qquad \text{eq. 5a}$$

Therefore from equation 4 it follows:

$$b_\nu = \sum_\nu d_{\nu-i} p_\nu = \begin{matrix} 1 \text{ for } i = 0 \\ 0 \text{ for } i \neq 0 \end{matrix}; i = -N,\ldots,-1,0,1,\ldots,+N \qquad \text{eq. 6}$$

If the value of $\nu$ becomes sufficiently high, $p_\nu$ tends to become zero due to the finite width of the sound beam. By experience it is known that $d_\nu$ follows the same rule. Therefore, the infinite system of equation 6 can be replaced by a finite system of the form:

$$b_\nu = \sum_{\nu=-N}^{+N} d_{\nu-i} p_\nu = \begin{matrix} 1 \text{ for } i = 0 \\ 0 \text{ for } i \neq 0 \end{matrix}; i = -N,\ldots,-1,0,1,\ldots,+N \qquad \text{eq. 7}$$

This is a system of $2N + 1$ equations with $2N + 1$ unknown elements. In this equation, $$d_{\nu-1} = 0 \text{ for } |\nu-1| > N$$

Figure 4:
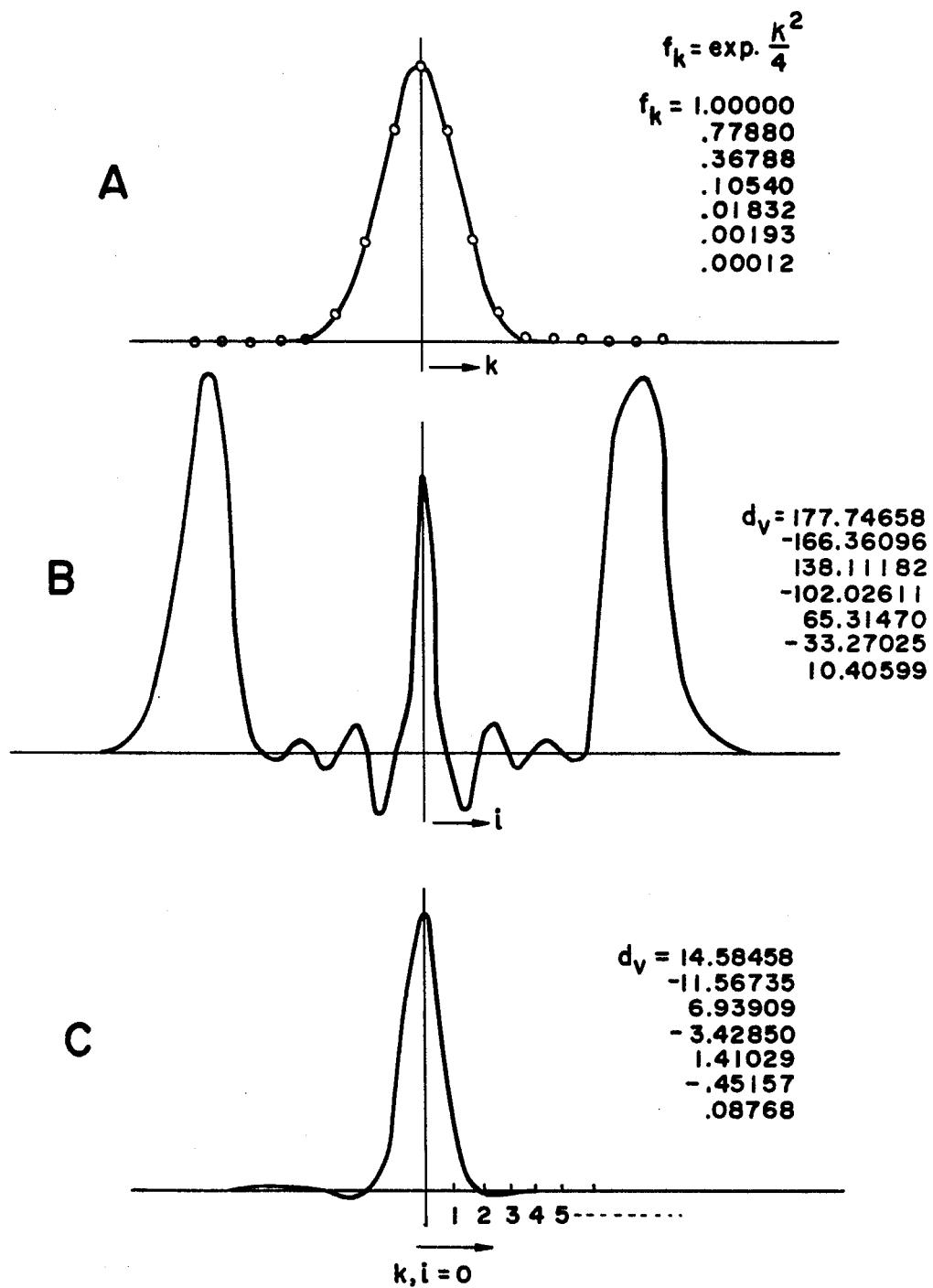
FIGS. 4A–4C are graphical representations of solutions of the equations per the invention.

To reduce calculation time N should be set as low as possible, but if N is set too low the graphs of $b_\nu$ are distorted as shown in FIG. 4B. If such a distorted graph occurs, the value N must be selected higher.

In the case of a symmetrical beam profile $p_{-\nu} = p_{+\nu}$ equation 7 is reduced to:

$$b_\nu = \sum_{\nu=0}^{N} (d_{\nu-i} + d_{\nu+i}) p_\nu = \begin{matrix} 1 \text{ for } i = 0 \\ 0 \text{ for } i \neq 0 \end{matrix} \qquad \text{eg. 7a}$$

This system contains only $N + 1$ equations.

The result of a computer test run is depicted in FIG. 4A showing the beam profile, which is assumed to follow a Gaussian curve of the form $f_k = \exp k^2/4$, together with the printout of the equation 7 is reduced to:

$$b_\nu = \sum_{\nu=0}^{N} (d_{\nu-i} + d_{\nu+i}) p_\nu = \begin{matrix} 1 \text{ for } i = 0 \\ 0 \text{ for } i \neq 0 \end{matrix} \qquad \text{eg. 7a}$$

This system contains only N + 1 equations.

The result of a computer test run in depicted in FIG. 4A showing the beam profile, which is assumed to follow a Gaussian curve of the form $f_k = \exp k^2/4$, together with the printout of the $f_k$ sequence. With $f_v = p_v$ the $d_v$ sequence (tabulated at the right side of graph 4B) was calculated from equation 7a setting $N = 6$. Equation 7 was solved using a Wang 700 computer with software program 1003/MA3. The $d_v$ sequence per FIG. 4B together with the $f_k$ sequence per FIG. 4A gives the $b_i$ sequence after deconvolution with the aid of equation 4. The $b_i$ sequence is plotted on the left hand side of FIG. 4B.

FIG. 4B shows, that the calculation is correct for $i = 0, 1, \ldots, 6$, but there is a maximum at $i = \pm 8$, and for less than 6 there are oscillations. This ringing interference vanishes if N, in equation 7a, is increased to 12 or higher (not shown here).

Another possibility to reduce the ringing interference per FIG. 4B without the need for more computer time is shown in FIG. 4C. In this computer run, in equation 7a, $i = 1$ was deleted and instead the value $i = 7$ was added. These equations are solved in the same computer time as in the example before. The $d_v$ sequence for this case is listed at the right of FIG. 4C and to the left the deconvolution sequence is shown. It will be noted that the ringing interference pattern vanishes (without the need of calculating more equations) by this method. The lateral resolution is not the best achievable, but it is much better than without using the described method (compare FIG. 4A).

In the prior art there are described other solutions for the deconvolution problem, but all require much more computer time. For example, R. Gold in TID-Report No. 18304 shows a method of iterative approximations. Several authors recommend calculating the Fourier Transform P ($\xi$) of the beam profile $p(x)$ and retransforming by inverse Fourier Transform 1/P ($\xi$). The resultant $d(x)$ corresponds to the $d_v$ sequence above.

The present method provides a solution for the deconvolution using less computer computation time. The time savings achieved become significant when applied to a real-time medical ultrasonic scanning apparatus as well be explained hereinafter.

Figure 5:
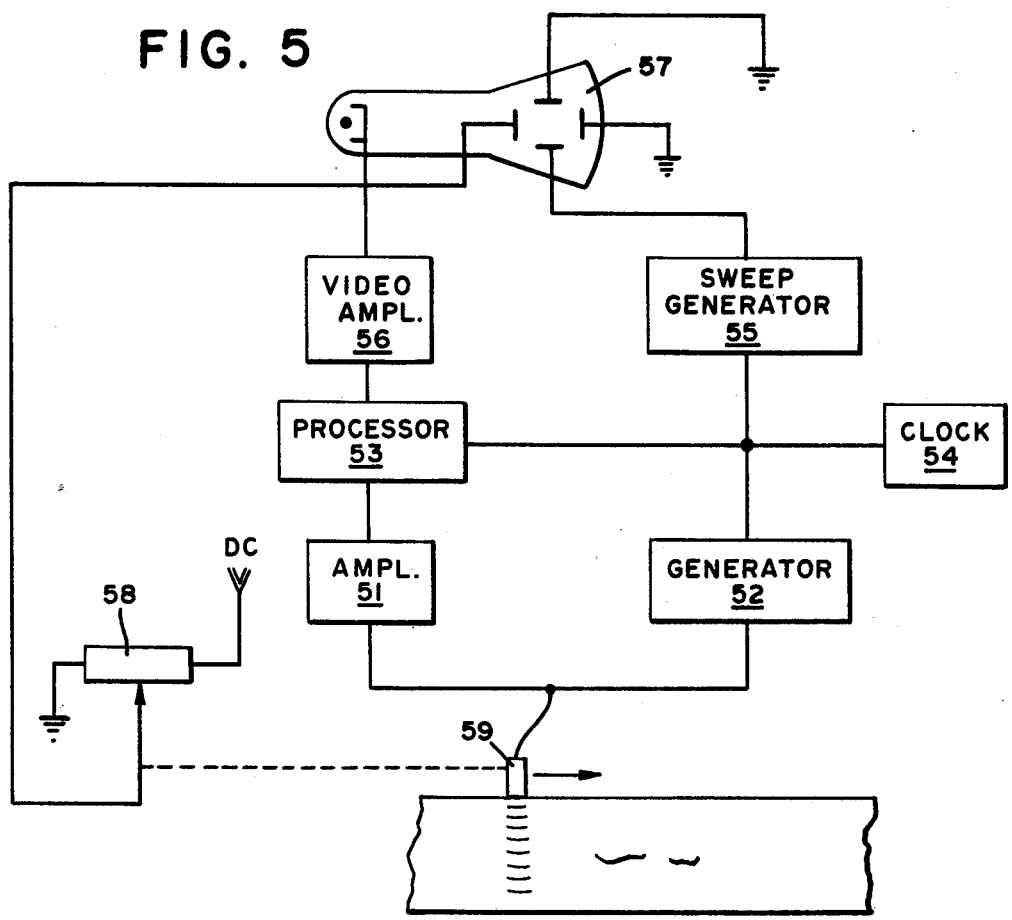
FIG. 5 is a schematic electrical circuit block diagram of an apparatus for practicing the present invention.

B-scan representations are produced, as is known, by moving a test probe, see FIG. 1A, slowly along an object (patient) to be examined and a device per FIG. 5 causes the object to be properly presented to scale on the screen of a cathode ray tube. Many similar methods are known and in use, all of which show the fundamental operation and follow the construction disclosed in FIG. 5. The "deconvolution method" described herein is transferable also to such variations. The most important variation comprises the use of a linear array transducer probe, for instance, a plurality (typically 100) of closely spaced transducer elements disposed in a linear array instead of a single probe undergoing physical motion. Rather than physically positioning the transducer 59 in FIG. 5, usually an electronic switching device comprising a step generator 58a and switching means 58b is coupled between the receiver amplifier 51 and the transmit pulse generator 52 and the test probe scan array 59a, 59b, 59c, etc., respectively to cause the elements of the array to be actuated in sequence. The switching device is controlled by a clock generator 54. A further important variation comprises a sector scan in which the test probe 59 does not undergo translational motion, but rather undergoes an angular oscillating motion. Still further modifications, are in use as are known to those skilled in the art in which the mechanical probe motion is replaced by an electronic beam scan applied to the probe to enable the probe to remain stationary while moving the beam.

The mode of operation of the circuit per FIG. 5 applies generally to all of the embodiments. A clock generator 54 produces timing pulses to the transmit pulse generator 52 as well as to the sweep generator 55 operated in synchronism with the clock generator 54. The repetition frequency is generally in the range between 500 Hz and 20 kHz, and a typical repetition frequency is approximately 1 kHz. The sweep generator 55 causes a signal to be manifest on the screen of the cathode ray tube 57 along the vertically disposed time axis. A position determining device 58, in the simplest case a potentiometer, is mechanically coupled to the test probe 59. In this manner lateral motion of the test probe along the surface of the object, along the X-axis, is transmitted to the tube 57 corresponding to the location of the probe along the surface of the object. An amplifier 51 amplifies the echo responsive signals received by the probe 59 and, as known, provides the amplified electrical signals via a video amplifier 56 to the brightness control electrode of the cathode ray tube 57. In accordance with the present invention a data processing device 53, as will be explained below, is series coupled in the video circuit for the purpose of subjecting the sequential echo signals $f_k$ from the amplifier to the deconvolution process.

Figure 5A:
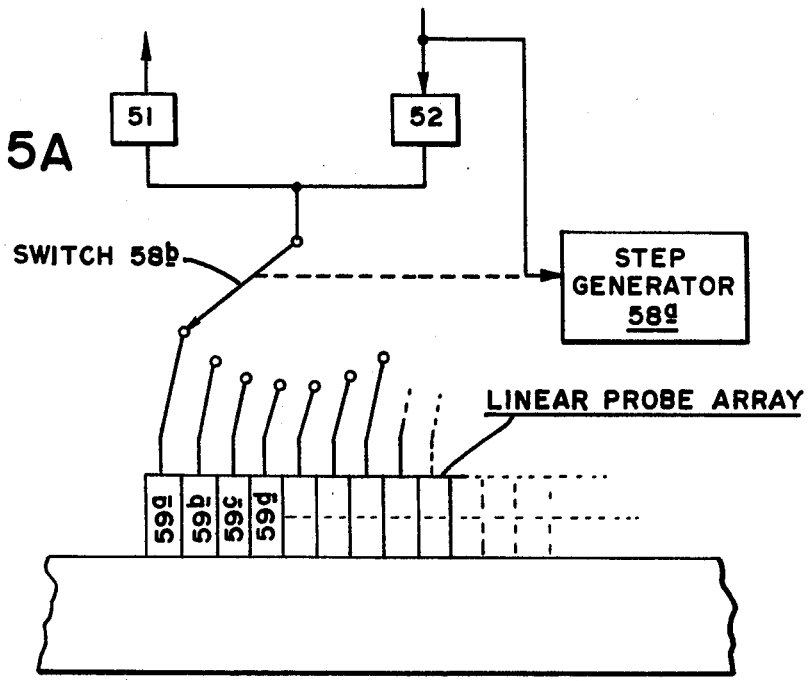
FIG. 5A is a schematic electrical circuit block diagram of a preferred embodiment of a portion of the circuit per FIG. 5.

The embodiment using a linear array is depicted in FIG. 5A. In this embodiment the probe 59 is replaced by the array of elements 59a, 59b, 59c, etc., which are energized in sequence by an electronic switch 58b in synchronism with the clock frequency 54. The position determining device 58 is replaced by a staircase generator 58a which provides in synchronism with the sequential switching of the elements a staircase output voltage signal, the latter signal being used for controlling the X-axis of the cathode ray tube 57. Aside from the above, the other functions remain identical as described in FIG. 5.

The following description deals with the data processor 53 which is necessary for performing the function comprising the present invention. In order to simplify the following description it is assumed that for providing a B-scan presentation an array probe per FIG. 5A having 64 elements is used, the elements are spaced from each other by 1.56 mm to provide an array 100 mm long. For the remaining parameters the following is assumed: the cathode ray tube screen 57 shows a B-scan display having a dimension of 100 mm by 100 mm, wherein the display is divided into 64 picture elements per column along the y-direction (time axis). Hence, the vertical resolution $\Delta Y$ is limited to $100/64 = 1.56$ mm. If a better resolution is desired, a finer division must be chosen. The following numerical data represents typical parameters.

Assuming for instance that a steel workpiece having an acoustic velocity $c = 5900$ m/sec (5.9mm/$\mu$sec) is to be scanned, then the input of the processor 53 is fed with a new amplitude value $f_k$ every $2 \times \Delta Y/c = 0.53 \mu$sec (transit time for the signal to traverse twice the depth increment). Commercially available and reasonably priced small process computers are incapable of calculating the value of $b_i$ per equation 4 in this short time interval. Therefore, the deconvolution problem could not heretofore be solved in real time.

If, however, real time operation is not required the problem can readily be solved using a miniprocessor by sequentially providing the signals from amplifier 51 via an analog-to-digital converter to the core memory of the processor for storage. This step is accomplished within 0.53μsec per $f_k$ value, thus obviating a further buffer storage means. The values of $d_v$ obtained during test are stored in a further part of the core memory. In the ensuing program sequence values of $b_i$ are calculated using the values of $f_k$ and $d_v$ per equation 4 and stored.

Thereafter the $b_i$ storage is interrogated in sequence and coupled via a digital-to-analog converter to the video amplifier 56. The output signals from the video amplifier 56 are provided to the writing electrode of the cathode ray tube.

With respect to the sequence of values $d_v$ it will be noted that for each depth increment, i.e. for each 1.56 mm portion of the B-scan presentation, a new value for $d_v$ must be obtained. Practice has shown, however, that measurements can be reduced, for example, by deriving a new $d_v$ sequence for each four depth increments, i.e., for each 4 × 1.56 mm = 6.25 mm. Therefore, measurements during the pretest operation and storage capacity in the computer can be saved. This fact can be utilized in the real-time solution described hereafter. Moreover, it should be mentioned that in several commercially available B-scan representation apparatus a preamplifier 51 is used having a logarithmic gain characteristic. This feature is advantageous since a logarithmic amplifier has a greater dynamic range than a linear amplifier. The output signal from the logarithmic amplifier is not the amplitude sequence $f_k$, but rather is log $f_k$. The computer must convert this value back to $f_k = 10^{\log f_k}$ which is possible with suitable software programs available for almost all process computers. In order to conserve computing time it is advantageous in the present case to store instead of the sequence $d_v$ the sequence log $d_v$ and instead of forming the product $d_v f_k$ to form the sum log $d_v + \log f_k$ and then converting this sum. This method requires less computer time. Also the special processors for real-time operation described hereafter are operated in a manner to partially utilize this computing shortcut.

The reason for the lengthy computing time of commercially available process computers resides in the fact that these computers are designed for series operation, that is, with respect to equation 4 each multiplication and summation are performed seriatim in time. In the following description a respective digital computer shown in FIG. 6 and an analog computer shown in FIG. 7 are described each of which performs the calculation required by equation 4 in parallel, i.e. simultaneously. Therefore, the computing time required is less than 0.3μsec and, hence, the equation 4 can be solved in real-time. Both computers comprise commercially available components, the analog computer per FIG. 7 is somewhat less expensive, but the digital computer per FIG. 6 has the advantage of greater long term stability.

Figure 6:
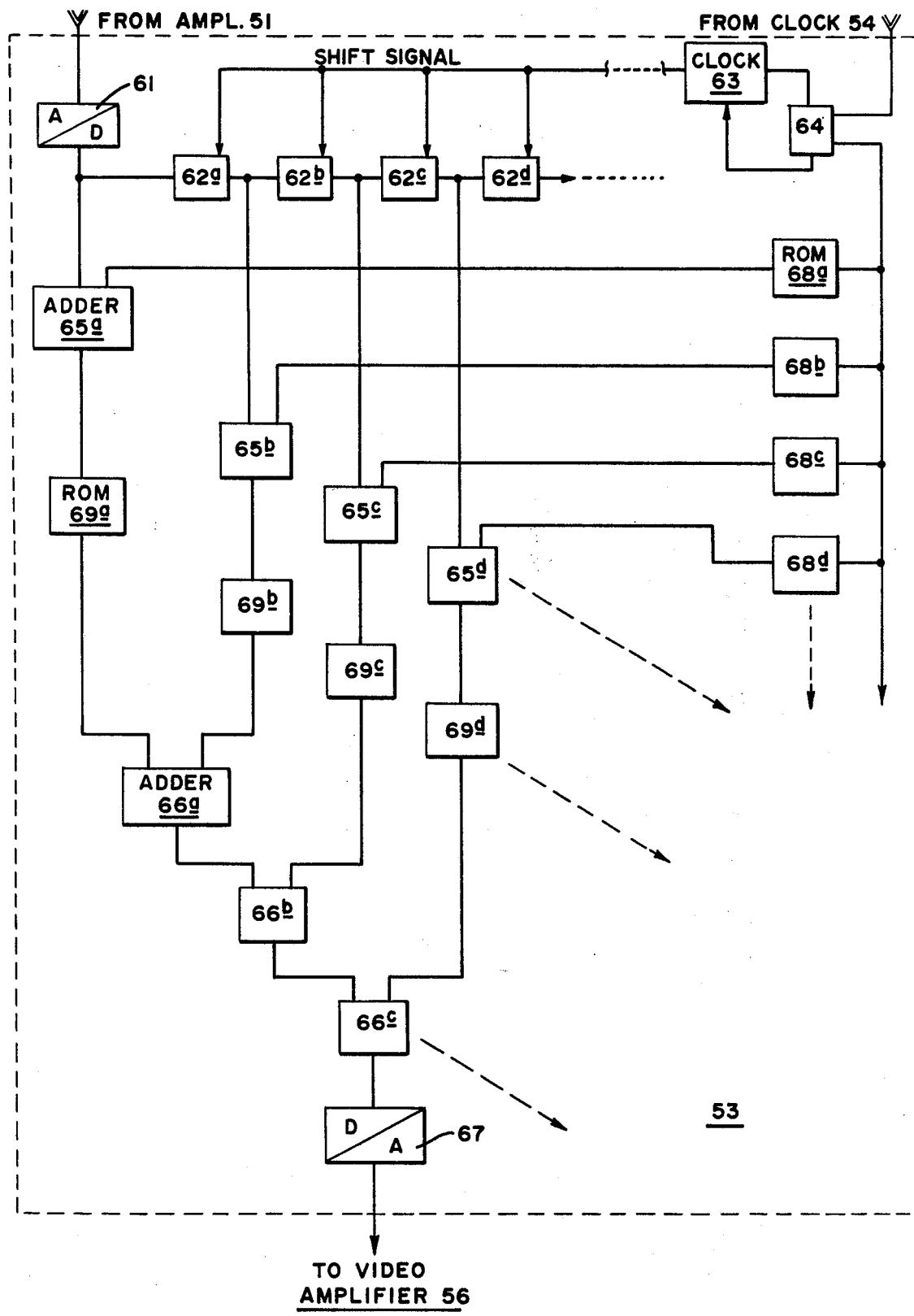
FIG. 6 is a preferred embodiment of a digital processor for practicing the invention.
Figure 7:
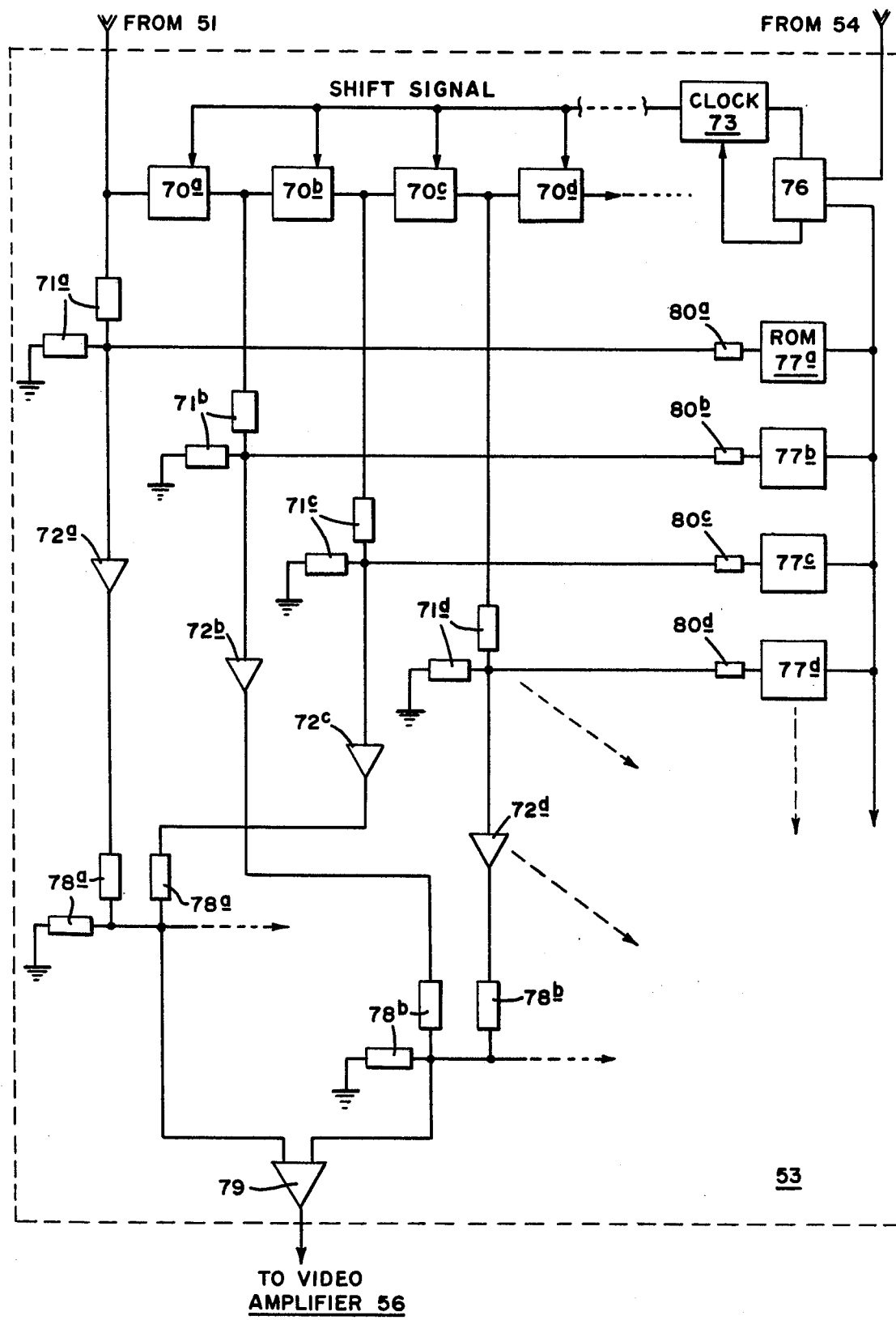
FIG. 7 is a preferred embodiment of an analog processor for practicing the invention.

With reference to FIG. 6, the amplitude values of log $f_k$ from the logarithmic amplifier 51 are transformed by the analog-to-digital converter 61 of the digital computer to an 8-bit binary word. If the process starts at the upper left hand corner of the B-scan presentation, the log $f_0$ values for the first column of the B-scan are provided to the converter 61 one after the other. These values are fed to a 64-position shift register 62a. The clock generator 63 shifts the shift register every $\Delta v = 0.53\mu$sec by one step to cause after 64 steps the value log $f_0$ for the first line of the display to appear at the last position of the register 62a and at the beginning of the register 62a the value of log $f_0$ for the last segment of the line. The clock pulses from generator 63 are counted simultaneously in a 6-bit binary counter 64. After the 64th step the counter provides an overflow signal which is used to stop the clock generator 63 and to inhibit further $f$-signals from being entered into the shift register 62a. This stand-by condition remains until a new start signal to the transmit pulse generator 52 is provided by the clock generator 54 for the B-scan presentation apparatus, such start signal denotes the beginning of a new line for constructing the B-scan presentation. This start signal is utilized also to reset the counter 64 to zero, causing the overflow condition to disappear. Hence, the clock generator 63 provides a further sequence of shift signals for the shift registers 62a, 62b, 62c, etc. The programmed pause maintains the correct synchronization of the computer with the transmit pulse of the B-scan presentation picture.

After receipt of the first clock signal of the new 64-series, the value of log $f_1$ for the next line is present at the input of shift register 62a, and the value of log $f_0$ for the first line is present at the input of shift register 62b. After a further sequence of 64 steps, the values log $f_2$, log $f_1$ and log $f_0$ are at the input of respective shift registers 62a, 62b, and 62c. In order to solve equation 4, 2N (see equation 7) 64-position shift registers must be provided to cause at the start of the 2N + 1st 64-series clock pulse signals from clock 63 all the values of log $f_k$ required in equation 4 to be available seriatim to the extent that $f_k$ is not zero. The following clock pulses produce the corresponding values for the 2nd, 3rd through the 64th line of the B-scan representation. After the next 64th series, the sequences log $f_{2N+1}$ until log $f_1$ appear sequentially for all lines and so forth.

The values of log $f_k$ available at the output of the shift registers are fed to the eight A-inputs ($A_1$, $A_2$ to $A_8$) of an 8-bit parallel adder. The B-inputs of these adders receive signals from the ROMs 68a, 68b, 68c, etc. These ROMs are addressed by the four most significant bits of the six-bit counter 64 to cause after every four clock pulses a new address. The ROMs 68a, 68b, 68c, etc., are programmed to cause for each address value (log $d_{-N}$, log $d_{-N+1}, \ldots,$ log$_N$) a respective log $d_v$ value to be provided in the form of an 8-bit binary word at the output.

Therefore, the sum log $d_{-N} + \log f_k$, log $d_{-N+1} + \log f_{k+1}$, etc., is provided at the output of the adders 65a, 65b, 65c, etc., in the form of an 8-bit binary word.

This value serves as address A for ROMs 69a, 69b, 69c, etc. These ROMs are programmed in a manner to cause for positive values of $d_v$ at the output the value $10^A (= d_{-N}f_k)$ as an 8-bit binary word. For the ROMs associated with a negative $d_v$ (i.e. $d_{-3}, d_{-1}, d_1, d_3, d_5, \ldots$) the 2's complement of $10^A$ is programmed to take into account the negative prefix of the product $d_v f_k$ as is customary in computer technique.

After forming the products $d_v f_k$ the output values of 2N + 1 ROMs 69a, 69b, 69c are added stepwise in 8-bit parallel adders 66a, 66b, 66c, etc., as shown in FIG. 6, to cause in the last adder (66c, FIG. 6) the $b_i$ value to appear in sychronism with the input values of log $f_k$, specifically the 64 values of $b_i$ for the respective first, second, third . . . column appear consecutively.

The output values $b_i$ are then converted via a digital-to-analog converter 67 to an analog signal and supplied to the video amplifier 56.

The analog computer circuit per FIG. 7 operates in accordance with the same computing principle as the digital computer circuit per FIG. 6, but most of the necessary digital components are replaced by the less expensive analog components. Fundamentally, the amplifier 51 is a logarithmic amplifier used in order to minimize the ensuing computing process. An analog to digital converter, corresponding to numeral 61 FIG. 6 is not necessary. The shift registers 70a, 70b, 70c, etc., provide the same function as shown in FIG. 6, however analog shift registers in accordance with the bucket-chain principle (for example SAM) are used. The functions of clock 73 and of block 76 are identical with FIG. 6. The 4 × 8 bit ROMs 77a, 77b, 77c, etc., are programmed for the values of 16 log $d_{-N}$; log $d_{-N+1}$ to log $d_N$ for the respective first, second, third, etc., group of four increments.

The resistive networks 71a, 71b, 71c, etc., together with networks 80a, 80b, 80c, etc., serve as adders for forming the sum log $f_k$ + log $d_v$ whereby the respective resistances associated with 80a, 80b, 80c, etc., are always in the ratio of 1:2:4:8, etc., to cause them to act simultaneously as digital-to-analog converters for the log $d_v$ values. The amplifiers 72a, 72b, 72c, etc., have exponential voltage gain characteristics to cause them to transform log $f_k$ + log $d_v$ into the product $f_k \cdot d_v$ which is necessary for further calculation. It is to be noted that the resistances 71a, 71b, 71c . . . are adjusted to cause the logarithmic amplifiers 72a, 72b, 72c to operate in their highly exponential portion of their characteristic. For the type 376 amplifier (Optical Electronics, Inc.) this range is between 400 to 700 mV. Thereafter, all of those products which have a $d_v$ having a positive subscript (even $d_v$) are added together in a resistance network 78a. The products associated with a $d_v$ having a negative subscript (odd $d_v$) are added in network 78b. Both sums are fed to a difference amplifier 79 to provide the difference signal to cause at the output of amplifier 79 the value $b_i$ in accordance with equation 4.

For both described specially designed computers various variations and combinations are possible. For instance, the shift register 62 in FIG. 6 can be replaced by an analog register, such as 70. The analog-to-digital converter 61 then must be disposed in circuit after the analog shift register. In FIG. 7 the linear amplifier can be modified by replacing adding circuits 71 by analog multipliers, the ROMs 77 storing $d_v$ instead of log $d_v$ and amplifiers 72 being linear amplifiers.

Typical components in the preferred embodiments of the processor 63 are:

| | |
|---|---|
| A/D Converter 61 | Micro Consultants Part No. An-DI 802 RAD |
| Shift Register 62a, 62b, etc. | Advanced Instruments AM 1506 |
| Binary Counter 64 and 76 | ITT MIC 7493 |
| Parallel Adder 65a, 65b, etc., and 66a, 66b, etc. | ITT MIC 7483 |
| ROM 68a, 68b, 68c, etc. ROM 69a, 69b, 69c, etc. ROM 77a, 77b, 77c, etc. | Monolithic Memories Part #5335 |

While several preferred embodiments of a computing means for use in a real time B-scan ultrasonic imaging system have been described and illustrated, further modifications and variations may be made without deviating from the broad principle and spirit of the invention which shall be limited solely by the scope of the appended claims.

What is claimed is:

1. An apparatus for improving the resolution of a real-time ultrasonic imaging system comprising:
   electroacoustic probe means adapted to be acoustically coupled to a workpiece;
   energizing means coupled to said probe means for causing said probe means to periodically transmit an ultrasonic energy search signal in the workpiece and to receive echo signals therefrom and to convert said echo signals into electrical signals;
   receiver means coupled to said probe means for receiving said electrical signals and providing respective discrete echo amplitude signals ($f_k$) responsive to said electrical signals, wherein $k$ is an integer and each signal $f_k$ is commensurate with a depth increment in the workpiece;
   processor means including storage means for storing a sequence of acoustic beam profile values ($d_v$) commensurate with the characteristics of said probe means coupled to said receiver means for sequentially receiving said amplitude signals ($f_k$), associating respective stored beam profile values ($d_v$) with amplitude signals ($f_k$) and providing a sequence of output signals $b_i$ commensurate with the equation:

$$b_i = \sum_k d_v \cdot f_k.$$

2. An apparatus as set forth in claim 1, and translating means coupled to said probe means for shifting the axis of said search signal relative to the workpiece.

3. An apparatus as set forth in claim 1, said probe means comprising an array of juxtaposed elements and said energizing means causing each of said elements to sequentially transmit a respective search signal.

4. An apparatus as set forth in claim 1, said storage means comprising read-only-memories.

5. An apparatus as set forth in claim 1, further including video amplifying means coupled to said processor means for receiving said sequence of output signals $b_i$ and in response thereto providing video signals, and display means coupled to said video amplifying means for providing a B-scan presentation responsive to said video signal.

6. An apparatus as set forth in claim 1, said receiver means including a logarithmic amplifier means for providing electrical signals commensurate with the logarithmic value of said respective discrete echo amplitude signals (log $f_k$) and said storage means storing said sequence of acoustic beam profile values as values of log $d_v$.

7. An apparatus as set forth in claim 6, said processor means comprising:
   an analog to digital converter coupled to said logarithmic amplifier means for converting said electrical signals commensurate with the logarithmic value to digital form;
   a clock for providing clock pulses, and
   shift register means coupled to said converter and said clock for sequentially receiving and shifting said digital form signals for storing said signals log $f_k$.

8. An apparatus as set forth in claim 7, said processor further comprising:

counting means coupled to said clock for receiving and counting the quantity of clock pulses provided and after counting a predetermined quantity of clock pulses providing an address signal to said storage means for providing a respective value log $d_v$ responsive to a respective address signal;

adding means coupled to said storage means and said shift register means for providing sum signals commensurate with the sums of the respective log $f_k$ signals and respective log $d_v$ signals;

conversion means coupled to said adding means for receiving said sum signals and converting respective said sum signals into product signals of the form $f_k \cdot d_v$, and additional adding means coupled to said conversion means for providing said sequence of output signals commensurate with the sum of said product signals.

9. An apparatus as set forth in claim 8, further including:

a digital to analog converter coupled to said additional adding means for providing said sequence of output signals as analog signals;

video amplifier means coupled to said digital to analog converter for receiving said analog signals and providing responsive thereto video signals, and display means coupled to said video amplifier for receiving said video signals and providing an image commensurate with said video signals.

10. An apparatus as set forth in claim 6, said processor means comprising:

a clock for providing clock pulses;

shift register means coupled to said receiver means and said clock for sequentially receiving and shifting said respective discrete echo amplitude signals;

counting means coupled to said clock for receiving and counting said clock pulses and providing after counting a predetermined quantity of clock pulses an address signal to said storage means;

logarithmic amplifier means coupled to said storage means and said shift register means for receiving respective shifted signals (log $f_k$) and stored values (log $d_v$) and providing respective product signals $f_k \cdot d_v$, and adding means coupled to said logarithmic amplifier means for receiving said product signals and providing said sequence of output signals.

11. An apparatus as set forth in claim 10, said adding means comprising:

means for providing a first signal commensurate with the sum of said product signals wherein $v$ is an even integer;

means for providing a second signal commensurate with the sum of said product signals wherein $v$ is an odd integer, and difference amplifying means for providing said sequence of output signals equal to the difference between said first signal and said second signal.

12. An apparatus as set forth in claim 10, further including:

video amplifier means coupled to said adding means for providing responsive to said sequence of output signals video signals, and display means coupled to said video amplifier for receiving said video signals and providing an image commensurate with said video signals.

13. An apparatus as set forth in claim 1, said processor associating a respective stored beam profile value $d_v$ with a plurality of amplitude signals $f_k$.

14. A real-time ultrasonic imaging system comprising:

clock means for providing timing pulses;

pulse generating means coupled to said clock means for providing responsive to said timing pulses trigger pulses;

electroacoustic probe means coupled to said pulse generating means for being energized responsive to said trigger pulses for periodically transmitting an ultrasonic energy search signal into a workpiece and for receiving echo signals therefrom and converting said echo signals into electrical signals;

receiver means coupled to said probe means for receiving said electrical signals and providing respective discrete echo amplitude signals ($f_k$) responsive to said electrical signals, wherein $k$ is an integer and each signal $f_k$ is commensurate with a depth increment in the workpiece;

computing means including storage means for storing a sequence of acoustic beam profile values ($d_v$) commensurate with characteristics of said probe means coupled to said receiver means for sequentially receiving said amplitude signals ($f_k$), associating respective stored beam profile values ($d_v$) with amplitude signals ($f_k$) and constructed to operate in the time interval between successive timing pulses for providing a sequence of output signals $b_i$ in accordance with the equation $$b_i = \sum_k d_v \cdot f_k,$$

and display means coupled to said computing means for receiving said sequence of output signals and displaying said output signals as a real-time image.

* * * * *